United States Patent
Mizushima et al.

(10) Patent No.: US 9,539,248 B2
(45) Date of Patent: Jan. 10, 2017

(54) AGENT FOR AMELIORATING CHRONIC OBSTRUCTIVE PULMONARY DISEASE

(71) Applicant: LTT BIO-PHARMA CO., LTD., Minato-ku, Tokyo (JP)

(72) Inventors: Toru Mizushima, Tokyo (JP); Hongxing Liu, Tokyo (JP)

(73) Assignee: LTT Bio-Pharma Co., Ltd., Tokyo (JP)

( * ) Notice: Subject to any disclaimer, the term of this patent is extended or adjusted under 35 U.S.C. 154(b) by 0 days.

(21) Appl. No.: 14/720,347

(22) Filed: May 22, 2015

(65) Prior Publication Data
US 2015/0250779 A1 Sep. 10, 2015

Related U.S. Application Data

(62) Division of application No. 14/385,067, filed as application No. PCT/JP2013/055476 on Feb. 28, 2013.

(30) Foreign Application Priority Data

Mar. 14, 2012 (JP) ................................. 2012-057704

(51) Int. Cl.
   A61K 31/452   (2006.01)
   C07D 211/46   (2006.01)
   A61K 9/00     (2006.01)
   A61K 9/20     (2006.01)

(52) U.S. Cl.
   CPC ............. *A61K 31/452* (2013.01); *A61K 9/007* (2013.01); *A61K 9/0031* (2013.01); *A61K 9/0053* (2013.01); *A61K 9/0078* (2013.01); *A61K 9/2018* (2013.01)

(58) Field of Classification Search
   CPC .... C07D 211/46; A61K 31/452; A61K 9/2018
   USPC ................................. 546/222; 514/327; 5/327
   See application file for complete search history.

(56) References Cited

U.S. PATENT DOCUMENTS

| | | | |
|---|---|---|---|
| 2,918,408 A | 12/1959 | Biel et al. | |
| 5,612,053 A * | 3/1997 | Baichwal | A61K 9/146 424/434 |
| 7,294,650 B2 | 11/2007 | Biggadike | |
| 7,482,371 B2 | 1/2009 | Rovati et al. | |
| 2007/0243260 A1* | 10/2007 | Snape | A61K 31/00 424/489 |
| 2008/0004247 A1 | 1/2008 | Lindmark et al. | |
| 2008/0020048 A1* | 1/2008 | Snape | A61K 31/00 424/489 |
| 2008/0066739 A1* | 3/2008 | LeMahieu | A61M 11/041 128/200.14 |
| 2009/0202514 A1 | 8/2009 | Yoneyama et al. | |

FOREIGN PATENT DOCUMENTS

| | | | |
|---|---|---|---|
| DE | 4219659 | * | 12/1993 |
| JP | 2006-56890 A | | 3/2006 |
| JP | 2008-506674 A | | 3/2008 |
| JP | 2008-189667 A | | 8/2008 |
| WO | WO 2009/142589 A1 | | 11/2009 |

OTHER PUBLICATIONS

Cantil , Drug.com, p. 1 (2015).*
Koning "Dry powder . . . " thesis, p. 1-13 (2001).*
Ochillo et al. "Atropine and mepenzolate . . . " Res. Comm. Chem. Pathology and Pharm. v.36(3) 503-6 (1982).*
Synergy, Medical Dictionary p. 1 (2015).*
International Search Report dated Apr. 9, 2013 with English translation (four (4) pages).
Japanese-language Written Opinion (PCT/ISA/237) dated Apr. 9, 2013 (three (3) pages).
Snider, "Chronic Obstructive Pulmonary Disease: Risk Factors, Pathophysiology and Pathogenesis," Annual Reviews Inc., 1989, vol. 40, pp. 411-429.
"Digestion & Absorption," 2005, vol. 28, No. 1 (five (5) pages).
Barnes et al., "COPD: current therapeutic interventions and future approaches," 2005, pp. 1084-1106, vol. 25, ERS Journals Ltd.
Belmonte, "Cholinergic Pathways in the Lungs and Anticholinergic Therapy for Chronic Obstructive Pulmonary Disease," Proc. Am. Thorac. Soc., 2005, vol. 2, pp. 297-304.
"The Lung perspectives," 2008, pp. 53-56, vol. 16, No. 1.
Mayo Clinic, 2007—http://www.mayoclinic.org/drugs-supplements/anticholinergics-and-antispasmodics-oral-route-parenteral-route-rectal-route-transdermal-route/description/drg-20070312?p=1.
Peter J. Barnes The American Journal of Medicine Supplement 2004, 117, pp. 24s-32s.

* cited by examiner

*Primary Examiner* — Celia Chang
(74) *Attorney, Agent, or Firm* — Crowell & Moring LLP

(57) ABSTRACT

This invention provides a safe and effective agent for ameliorating chronic obstructive pulmonary disease (COPD) that has both a bronchodilator effect and an anti-inflammatory effect. The agent for ameliorating chronic obstructive pulmonary disease contains mepenzolate bromide as an active ingredient. More preferably the mode of administration of the agent for ameliorating chronic obstructive pulmonary disease is airway administration or inhalation administration, and furthermore the mode of administration thereof is oral administration or rectal administration. This invention is a safe and effective agent for ameliorating chronic obstructive pulmonary disease (COPD) that has both a bronchodilator effect and an anti-inflammatory effect of mepenzolate bromide.

4 Claims, 13 Drawing Sheets

AGENT FOR AMELIORATING CHRONIC OBSTRUCTIVE PULMONARY DISEASE

CROSS REFERENCE TO RELATED APPLICATIONS

This application is a divisional of U.S. application Ser. No. 14/385,067, filed Sep. 12, 2014, which is a National Stage application of PCT International Application PCT/JP2013/055476, filed on Feb. 28, 2013, which claims priority from Japanese Patent Application No. 2012-057704, filed on Mar. 14, 2012, the disclosures of which are expressly incorporated by reference herein.

TECHNICAL FIELD

The present invention relates to an agent for ameliorating chronic obstructive pulmonary disease, and specifically to an agent for ameliorating chronic obstructive pulmonary disease that contains mepenzolate bromide (hereinafter may be referred to simply as "mepenzolate") as an active ingredient.

BACKGROUND ART

In recent years, bronchodilators (a β-agonist, a muscarinic antagonist, and the like) have been used for treatment of chronic obstructive pulmonary disease (COPD: chronic obstructive pulmonary disease, hereinafter may be referred to as "COPD") and these are reported to improve airflow limitation temporarily (Non-Patent Literature 1).

Furthermore, ipratropium bromide, which is a muscarinic antagonist, is reported to exhibit a bronchodilator effect by relaxing bronchial smooth muscle (Non-Patent Literature 2).

Chronic obstructive pulmonary disease (COPD) is a disease in which various factors, particularly smoking causes chronic lung inflammation and the inflammation causes alveolar destruction and bronchial mucous gland hypertrophy, which in turn lead to shortness of breath and increased coughing or expectoration.

A disease previously referred to as pulmonary emphysema (PE) and a disease previously referred to as chronic bronchitis (CB) are often combined in various ratios and developed, and accordingly, the diseases caused by these two diseases came to be collectively referred to as chronic obstructive pulmonary disease (COPD).

According to a trial calculation made by the World Health Organization (WHO), three million people died of COPD worldwide in one year in 2005 and COPD is the fourth leading cause of death, and it is predicted that the number of deaths from COPD will increase further by 30% in the next 10 years. According to statistics by the Ministry of Health, Labor and Welfare in Japan, in 2005, deaths from COPD accounted for 1.3% of the total number of Japanese deaths and COPD is the tenth leading cause of death and the seventh leading cause of death exclusively in men.

The primary cause of COPD development is smoking. 90% of COPD patients are smokers (Non-Patent Literature 3) and the risk of smokers developing COPD is six or more times higher than that by nonsmokers. Approximately 10 to 15% of smokers develop COPD and, exclusively in the elderly population, nearly 50% of smokers suffer from COPD. Other causes include indoor air pollution or air pollution, inhalation of chemical substances or dust, genetic factors, pneumonia or bronchitis in childhood, and the like.

COPD is a disease whose characteristic condition is airflow limitation, that is, difficulty in breathing out, although the true nature of the condition is chronic airway inflammation. Smoking, inhaled substances, and the like cause inflammation in various sites in a lung ranging from a central airway to a peripheral bronchus. It is believed that the inflammation leads to protease-antiprotease imbalance, oxidant-antioxidant imbalance, and the like, which in turn causes alveolar destruction and bronchial mucous gland hypertrophy.

COPD is an incurable disease since irreversible destruction of the airway has occurred. Smoking cessation, pharmacotherapy by administration of e.g., a bronchodilator, an expectorant, and an antitussive drug, oxygen therapy, or the like can only relieve symptoms of COPD, and thus COPD is a very troublesome disease.

From the above-mentioned point of view, various kinds of agents for ameliorating COPD or methods for ameliorating COPD have been proposed so far (for example, Patent Literatures 1 and 2); however, development of an even better agent for ameliorating COPD is currently awaited.

In the above-mentioned context, the present inventors have worked toward development of an agent for ameliorating COPD by performing a study to search existing commercially available drugs. As a result, the present inventors have confirmed that mepenzolate bromide, which has been used as a therapeutic drug for irritable bowel, exhibited a therapeutic effect on COPD based on a bronchodilator effect and an anti-inflammatory effect thereof, and thus accomplished the present invention.

Mepenzolate bromide is known as an anticholinergic drug that has an effect of suppressing movement and contraction in a lower gastrointestinal tract and has been used as a therapeutic drug for irritable bowel in a clinical setting since 1967. However, it is unknown that mepenzolate bromide is effective for COPD treatment.

Furthermore, there has been no known therapeutic agent for COPD that has both a bronchodilator effect and an anti-inflammatory effect so far.

PRIOR ART DOCUMENTS

Patent Literature

Patent Literature 1: Japanese Patent Application Laid-Open No. 2006-56890
Patent Literature 2: Japanese Patent Application Laid-Open No. 2008-189667

Non-Patent Literature

Non-Patent Literature 1: European Respiratory Journal, Vol. 25, p 1084-1106 (2005)
Non-Patent Literature 2: Proceedings of the American Thoracic Society, Vol. 2, p 297-304 (2005)
Non-Patent Literature 3: Annual Review of Medicine, Vol. 40, p 411-429 (1989)

SUMMARY OF THE INVENTION

Problems to be Solved by the Invention

Therefore, in view of the above-mentioned present circumstances, it is an object of the present invention to provide a safe and effective agent for ameliorating COPD that contains mepenzolate bromide as an active ingredient.

Means for Solving the Problem

To solve the above-mentioned problem, in a basic embodiment, the present invention provides an agent for ameliorating chronic obstructive pulmonary disease that contains mepenzolate bromide as an active ingredient.

More preferably, the present invention provides an agent for ameliorating chronic obstructive pulmonary disease whose mode of administration is airway administration or inhalation administration.

Furthermore, the present invention provides an agent for ameliorating chronic obstructive pulmonary disease whose mode of administration is oral administration.

The present invention also provides an agent for ameliorating chronic obstructive pulmonary disease whose mode of administration is rectal administration.

EFFECTS OF THE INVENTION

The present invention provides an agent for ameliorating COPD that contains mepenzolate bromide, which has already been used as a therapeutic drug for irritable bowel and whose safety has been confirmed, as an active ingredient.

Mepenzolate bromide, which is an active ingredient of the agent for ameliorating COPD provided by the present invention, has an excellent effect of ameliorating COPD, and in particular exhibits a significant effect by airway administration and inhalation administration. Furthermore, mepenzolate bromide showed an excellent effect by oral administration and rectal administration.

The effect of mepenzolate bromide is based on a bronchodilator effect and an anti-inflammatory effect. Since there has been, until now, no agent for ameliorating COPD that has both of these effects, the agent for ameliorating COPD of the present invention is a very specific agent for ameliorating COPD.

Furthermore, a feature of mepenzolate bromide, which is an active ingredient of the agent for ameliorating COPD provided by the present invention, is that it shows the effects thereof by an action mechanism different from those of a muscarinic antagonistic action and an anticholinergic action.

Therefore, in a situation where there has been, until now, no effective agent for ameliorating COPD, the specific and safe mepenzolate bromide can be administered to ameliorate the symptoms of COPD, and thus, the medical effect thereof is very specific.

EMBODIMENTS FOR CARRYING OUT THE INVENTION

Figure 1:
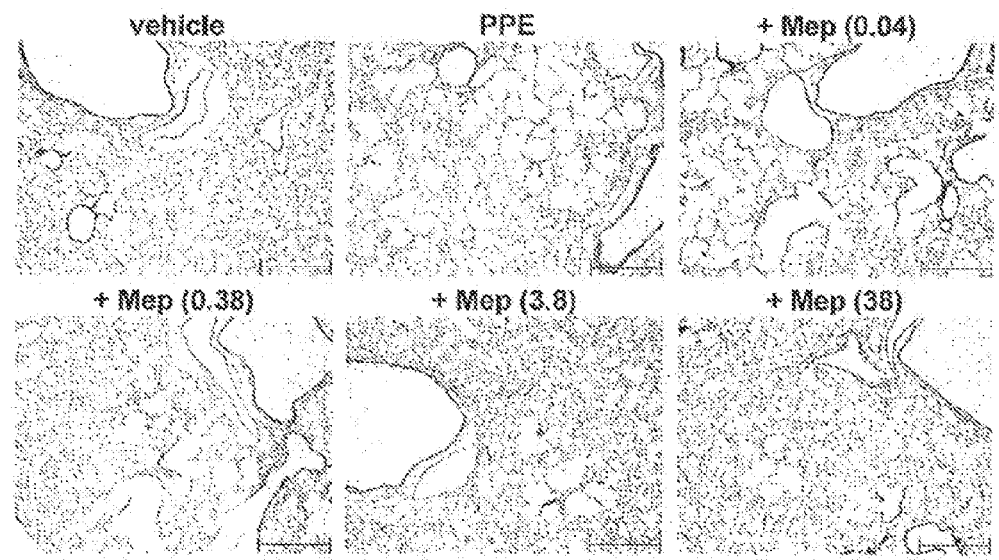
FIG. 1 shows electron micrographs of the lung tissues dyed with H&E in Test Example 1, in which mepenzolate bromide was administered via the airway.

Mepenzolate bromide used in the agent for ameliorating COPD provided by the present invention is a quaternary ammonium salt compound having the below-mentioned chemical formula.

This agent has already been on the market as a medicine. Therefore, a commercially available product can be used as an active ingredient of the agent for ameliorating COPD of the present invention as it is.

[Chemical formula 1]

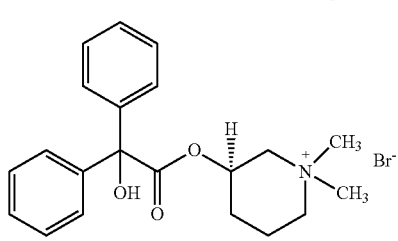

The agent for ameliorating COPD provided by the present invention contains mepenzolate bromide represented by the above-mentioned chemical formula as an active ingredient and can be administered preferably by airway administration and inhalation administration. Furthermore, the inventive agent can be effective by oral administration or rectal administration.

An airway-administered formulation for the above-mentioned airway administration and an inhalation formulation for the above-mentioned inhalation administration represent a pharmaceutical composition to be delivered to tissues such as a trachea, a bronchus, or a lung, and favorably represent a nasal drop or a composition suitable for transnasal administration or pulmonary administration. These formulations are effective when administered by a nebulizer, an atomizer, a dropper, a pipette, a cannula, and the like.

In such a case, the airway-administered formulation and the inhalation formulation can be prepared in the form of a powder formulation, a solution formulation, or a suspension formulation of mepenzolate bromide.

When the airway-administered formulation and the inhalation formulation are prepared as a powder formulation, the formulations can be prepared by processing mepenzolate bromide as an active ingredient into fine particles alone or together with a suitable additive such as an excipient, a lubricant, a binder, a disintegrant, a stabilizer, and a flavoring agent.

Furthermore, when the airway-administered formulation and the inhalation formulation are prepared as a solution formulation or a suspension formulation, the formulations can be prepared as follows. For example, the formulations can be prepared by dissolving or suspending mepenzolate bromide in water or a mixture that is a mixed solvent of water and a cosolvent, for example, an alcoholic cosolvent such as ethanol, propylene glycol, or polyethylene glycol.

Such solution or suspension may further contain an antiseptic, a solubilizer, a buffering agent, an isotonic agent, an absorption promoter, a thickener, and the like.

The airway-administered formulation and the inhalation formulation prepared as described above are administered to a nasal cavity or an oral cavity or directly to a tissue such as a trachea, a bronchus, or a lung by means common in the field of an inhalation formulation. For example, these formulations are administered by using a dropper, a pipette, a cannula, or a sprayer such as an atomizer or a nebulizer to pulverize the formulations.

When a sprayer is used, the formulations can be sprayed as an aerosol kept in a container under pressure with a suitable propellant (for example, chlorofluorocarbon such as dichlorofluoromethane, trichlorofluoromethane, or dichlorotetrafluoromethane, or gas such as carbon dioxide) or be administered by using a nebulizer.

When the agent for ameliorating COPD of the present invention is prepared as an oral formulation, a tablet, a powder, a granule, a capsule, and the like can be produced by adding an additive such as an excipient, a lubricant, a binder, a disintegrant, a stabilizer, and a flavoring agent to mepenzolate bromide as an active ingredient.

When an oral formulation is prepared, for example, a tablet can be prepared by using a usual tablet compression machine after adding an excipient such as lactose, starch or derivatives thereof, or cellulose or derivatives thereof; a binder such as carboxymethylcellulose sodium, alginic acid, or gum arabic; a lubricant such as magnesium stearate or talc; and other conventional additives as necessary.

When the agent for ameliorating COPD of the present invention is prepared as a formulation for rectal administration (an enema), the formulation may be in any form such as an aqueous solution form, a suspension form, a sol form, or a gel form. The formulation for rectal administration is prepared by using water, glycerol, ethylene glycol, propylene glycol, polyethylene glycol, polypropylene glycol, a vegetable oil, and the like as appropriate. Additionally, a thickener, a buffering agent, a preservative, a pH regulator, and the like may be added as appropriate.

The dosage of mepenzolate bromide that is an active ingredient of the agent for ameliorating COPD of the present invention varies depending on a method by which the formulation is prepared, a dosage form, a symptom of the disease, the age and weight of a patient, and the like and thus cannot be necessarily specified. However, by way of example, an appropriate clinical dosage is 0.5 to 200 mg per day for adults in the case of administration of an airway-administered formulation and an inhalation formulation and 0.5 to 500 mg per day for adults in the case of administration of an oral formulation. The frequency of administration cannot be necessarily specified, either. The frequency of administration can be once or several times a day.

In the case of administration of an enema, an appropriate dosage is 0.01 mg to 100 mg per day for adults.

Furthermore, mepenzolate bromide that is an active ingredient of the agent for ameliorating COPD of the present invention can be used more effectively by combined administration with an anticholinergic drug such as ipratropium, scopolamine, pirenzepine, tiotropium, or oxitropium.

EXAMPLES

Hereinbelow, the present invention will be described in more detail with reference to specific Test Examples and Working Examples, but the present invention is not limited to these descriptions.

"Mepenzolate" described in the below-mentioned Test Examples and Working Examples refers to mepenzolate bromide.

Furthermore, "PPE" described in the figures refers to porcine pancreatic elastase and "Mep" refers to mepenzolate.

The airway administration and inhalation administration, measurement of elastance, and measurement of $FEV_{0.05}$/FVC in the below-mentioned Test Examples were performed by the methods described below.

Airway Administration:

100 μg of porcine pancreatic elastase per mouse and different doses of mepenzolate were dissolved in 30 μL of phosphate buffered saline (PBS) per mouse and this solution was injected into the airway of a mouse anesthetized with chloral hydrate by a micropipette.

PBS alone was administered to a control mouse.

Inhalation Administration:

A mouse was placed in a chamber. Then, the whole amount of a mepenzolate solution prepared by dissolving mepenzolate in 10 mL of PBS was sprayed onto the mouse over 30 minutes by using an ultrasonic nebulizer (NE-U07, manufactured by OMRON Corporation) that was connected to the chamber.

PBS alone was sprayed onto a control mouse.

Each mouse was locked in the chamber for 10 minutes after spraying was completed.

Measurement of Elastance:

Lung function and airway resistance were measured by using a computer-controlled small animal ventilator (FlexiVent, SCIREQ Scientific Respiratory Equipment Inc.).

A mouse was anesthetized with chloral hydrate, a tracheostomy was performed, and an 8 mm metal tube was inserted into the trachea. Ventilation was performed on the mouse with a volume of 8.7 mL/kg, a positive end-expiratory pressure of 2 to 3 cmH$_2$O, and a respiratory rate of 150 times/min.

Total respiratory system elastance was measured by a snap shot technique and tissue elastance was measured by a forced oscillation technique.

Data analysis was conducted by using FlexiVent software.

Measurement of $FEV_{0.05}/FVC$:

Measurement of a ratio of forced expiratory volume (FEV) in the first 0.05 seconds to forced vital capacity (FVC) ($FEV_{0.05}/FVC$) was performed by using the above-mentioned computer-controlled small animal ventilator connected to a negative pressure reservoir (SCIREQ Scientific Respiratory Equipment Inc.).

$FEV_{0.05}/PVC$ was determined by using the FlexiVent software.

Test Example 1

Effect of Intratracheal Administration of Mepenzolate on Porcine Pancreatic Elastase-Induced Pulmonary Emphysema and Altered Lung Function <Method>

A lung damage model for pulmonary emphysema and altered lung function was generated by administering 100 μg of porcine pancreatic elastase per mouse to 4 to 6 week old ICR mice once via the airway.

Different doses of mepenzolate were administered to these mice via the airway (μg/kg) or by inhalation (μg/chamber) once daily for 14 days (Day 0 to Day 13) and the mice were euthanized on Day 14. Sections of the lung tissues were prepared and dyed with H&E (hematoxylin-eosin staining), and stained images were obtained by electron microscopy.

Figure 4:
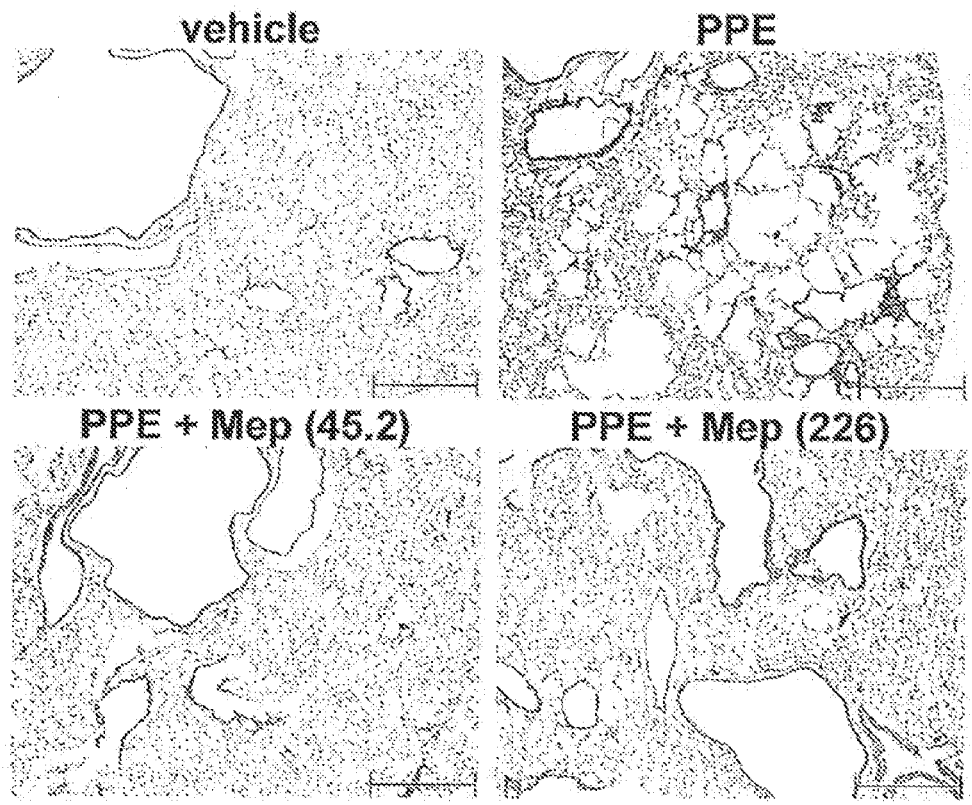
FIG. 4 shows electron micrographs of the lung tissues dyed with H&E in Test Example 1, in which mepenzolate bromide was administered by inhalation.

The results were shown in FIG. 1 (airway administration) and FIG. 4 (inhalation administration) (scale bar: 500 μm).

The airspace size in the cells in the H&E stained images obtained above was measured as a mean linear intercept (MLI; μm).

Figure 2:
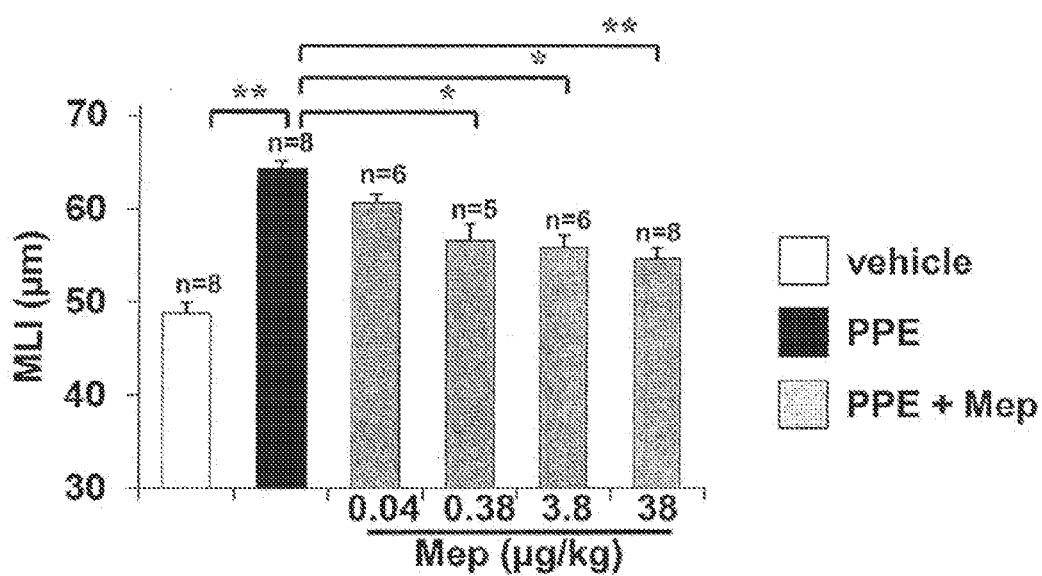
FIG. 2 shows a graph showing the results of measurement of a mean linear intercept in Test Example 1, in which mepenzolate bromide was administered via the airway.
Figure 5:
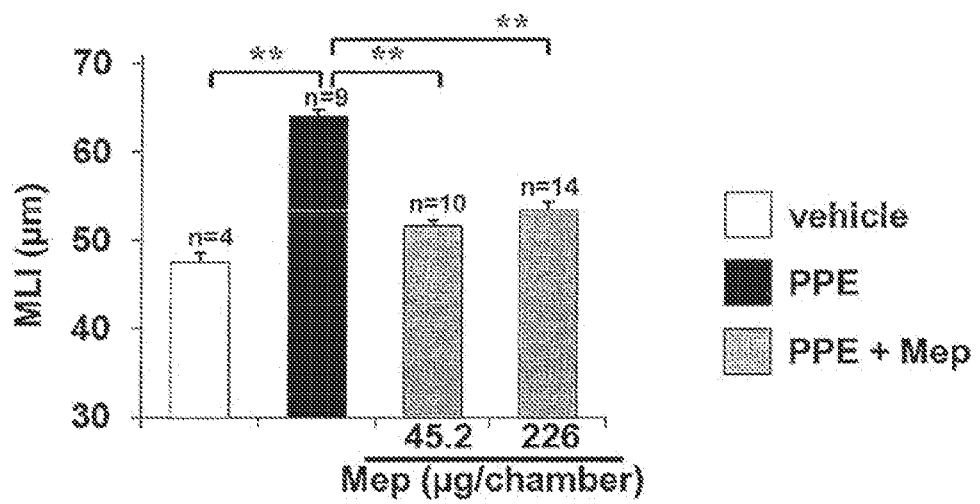
FIG. 5 shows a graph showing the results of measurement of a mean linear intercept in Test Example 1, in which mepenzolate bromide was administered by inhalation.

The results were shown in FIG. 2 (airway administration) and FIG. 5 (inhalation administration).

Then, on Day 14, the total respiratory system elastance and the tissue elastance were measured by the method described in the above-mentioned "Measurement of Elastance."

Figure 3:
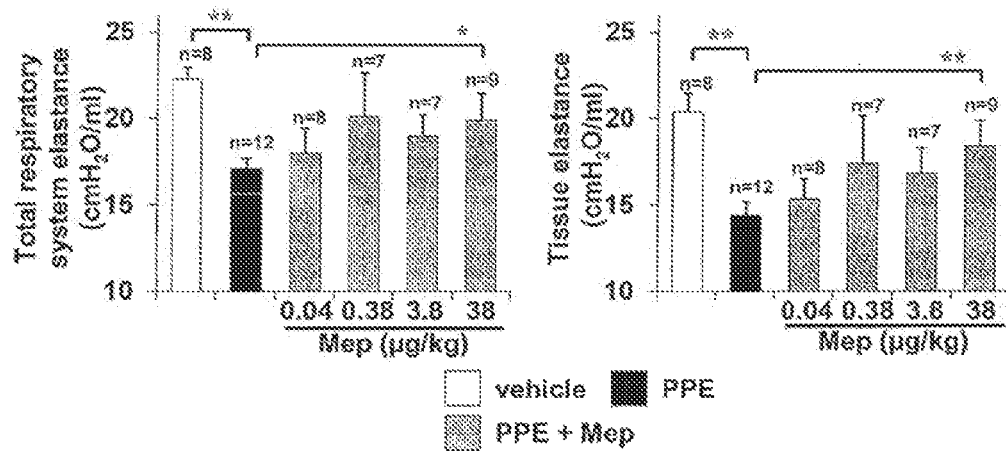
FIG. 3 shows graphs representing the results of measurement of total respiratory system elastance and tissue elastance in Test Example 1, in which mepenzolate bromide was administered via the airway.
Figure 6:
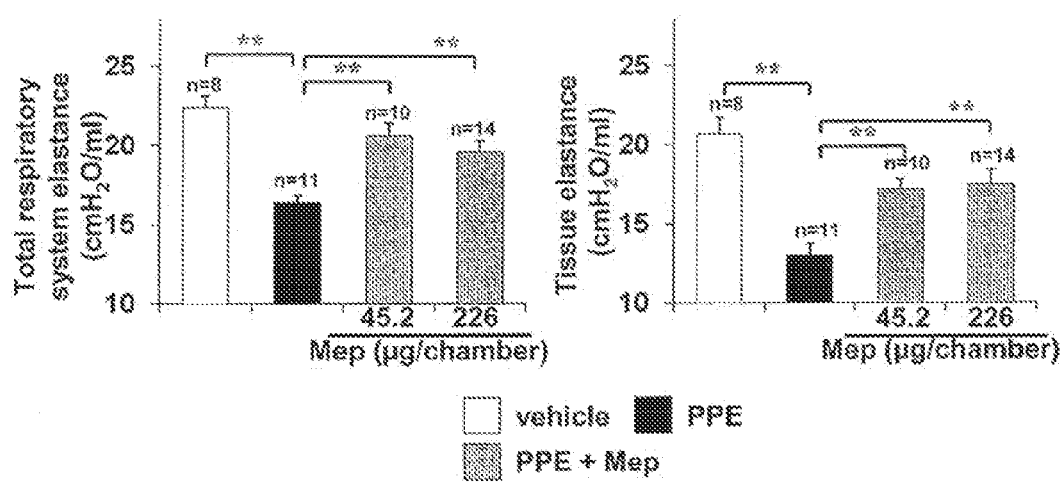
FIG. 6 shows graphs representing the results of measurement of total respiratory system elastance and tissue elastance in Test Example 1, in which mepenzolate bromide was administered by inhalation.

The results were shown in FIG. 3 (airway administration) and FIG. 6 (inhalation administration).

<Results>

As is found from the results shown in FIGS. 1 and 2 and FIGS. 4 and 5, the mean linear intercept was suppressed and damage in the alveolar wall was improved by both airway administration and inhalation administration of mepenzolate. Especially, inhalation administration had a slightly better suppressive effect.

As is found from the results shown in FIG. 3 and FIG. 6, the total respiratory system elastance and the tissue elastance were significantly improved by both airway administration and inhalation administration of mepenzolate.

It was found from the results described above that mepenzolate significantly improved damage in the lung induced by elastase by both airway administration and inhalation administration.

Test Example 2

Effect of Mepenzolate on Porcine Pancreatic Elastase Pretreatment-Induced Pulmonary Emphysema and Altered Lung Function <Method>

After 4 to 6 week old ICR mice were used and treated with porcine pancreatic elastase by a similar method to that in Test Example 1, different doses (μg/kg) of mepenzolate were administered to these mice via the airway once daily from 14 days to 20 days after the treatment. Then, the mice were euthanized, sections of the lung tissues were prepared and dyed with H&E, and stained images were obtained by electron microscopy.

Figure 7:
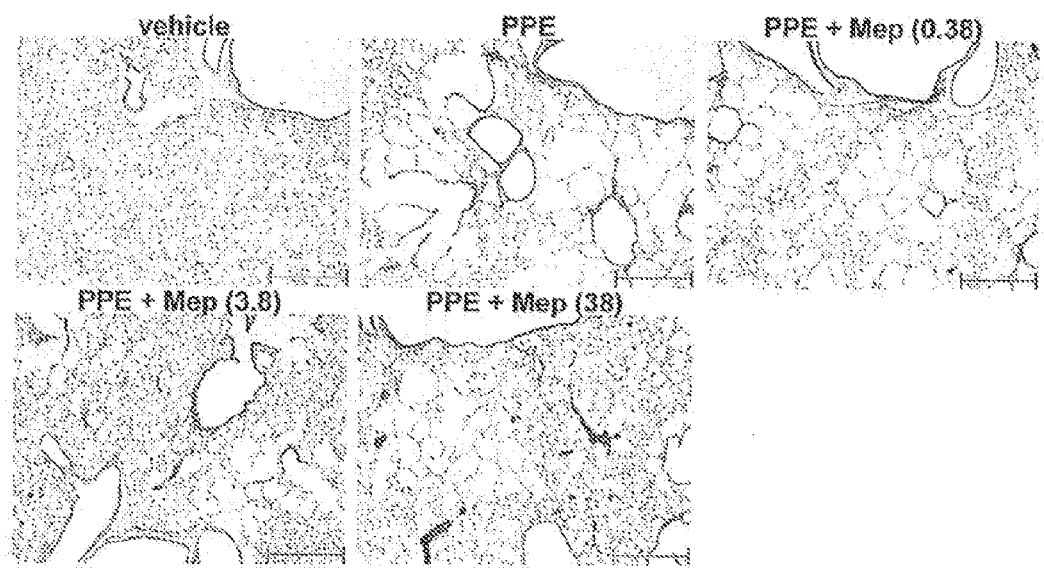
FIG. 7 shows electron micrographs of the lung tissues dyed with H&E in Test Example 2.

The results were shown in FIG. 7 (scale bar: 500 μm).

Subsequently, the airspace size in the cells in the obtained H&E stained images was measured as a mean linear intercept.

Figure 8:
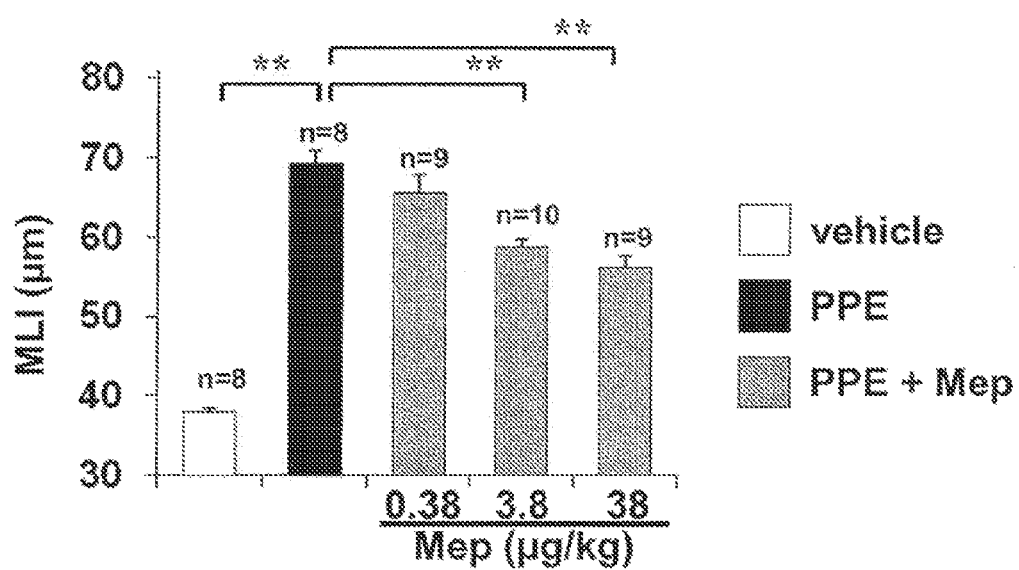
FIG. 8 shows a graph showing the results of measurement of a mean linear intercept in Test Example 2.

The results were shown in FIG. 8.

Then, on Day 21, the total respiratory system elastance and the tissue elastance were measured by a similar method to that in Test Example 1.

Figure 9:
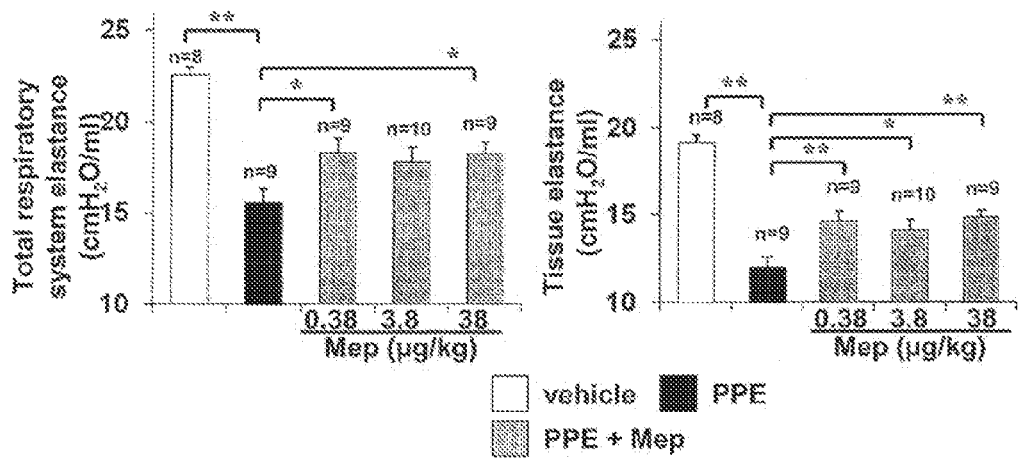
FIG. 9 shows graphs representing the results of measurement of total respiratory system elastance and tissue elastance in the case of airway administration in Test Example 2.

The results were shown in FIG. 9.

<Results>

As is found from the results shown in FIG. 7 and FIG. 8, the mean linear intercept was suppressed and damage in the alveolar wall was improved dose-dependently in the case of airway administration of mepenzolate. The mean linear intercept was increased compared to that in the case of coadministration in Test Example 1.

As is found from the results shown in FIG. 9, the total respiratory system elastance and the tissue elastance were significantly improved by airway administration of mepenzolate.

The results described above showed that airway administration of mepenzolate improved the mean linear intercept and the total respiratory system elastance and the tissue elastance in the mice having their lungs damaged by pre-administration of porcine pancreatic elastase.

Test Example 3

Effect ($FEV_{0.05}$/FVC) on Poor Lung Function Induced by Porcine Pancreatic Elastase Compared with Muscarinic Antagonist <Method>

As with Test Example 1, 4 to 6 week old ICR mice were treated with porcine pancreatic elastase. These mice received mepenzolate, ipratropium, scopolamine, or pirenzepine, each at 38 µg/kg by airway administration once daily for 11 days. On Day 14, $FEV_{0.05}$/FVC was measured by the method described in the above-mentioned "Measurement of $FEV_{0.05}$/FVC."

Figure 10:
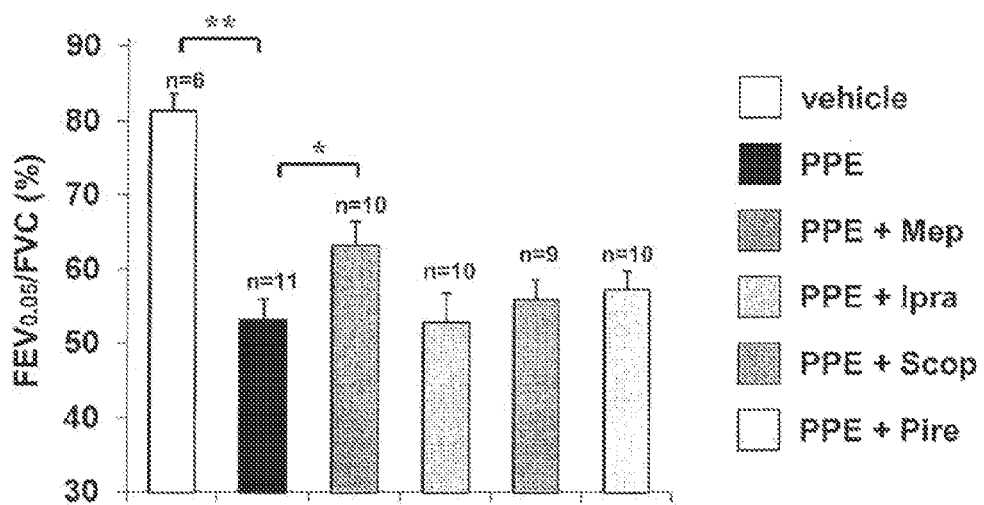
FIG. 10 shows a graph showing the results of measurement of $FEV_{0.05}/FVC$ in Test Example 3.

The results were shown in FIG. 10.

In the figure, "Ipra," "Scop," and "Pire" denote ipratropium, scopolamine, and pirenzepine, respectively.

<Results>

As is found from the results shown in FIG. 10, mepenzolate effectively exhibited a recovering effect of vital capacity represented by $FEV_{0.05}$/FVC that had been reduced by PPE administration. On the other hand, ipratropium (Ipra), scopolamine (Scop), and pirenzepine (Pire), which are existing drugs that have a muscarinic antagonistic action, did not show a significant recovering effect. All of mepenzolate, ipratropium, scopolamine, and pirenzepine are known to have a muscarinic antagonistic action (an anticholinergic action); however, ipratropium, scopolamine, and pirenzepine had no effect of $FEV_{0.05}$/FVC and only mepenzolate had an effect of $FEV_{0.05}$/FVC. This suggests that mepenzolate improves vital capacity by an action mechanism different from that of a muscarinic antagonistic action (an anticholinergic action).

Test Example 4

Effect of Mepenzolate on Methacholine-Induced Airway Constriction

<Method>

Increase in airway resistance induced by methacoline was measured. 4 to 6 week old ICR mice received 1 mg/mL methacoline by nebulization over 20 seconds and this was repeated five times. After administration of methacoline was completed, the airway resistance was measured by a snap shot technique. All the data were analyzed by using FlexiVent software.

Different doses (µg/kg) of mepenzolate were administered to the mice via the airway, and one hour after administration, the mice received five exposures to nebulized methacoline, and then, the airway resistance for each dose was measured.

Figure 11:
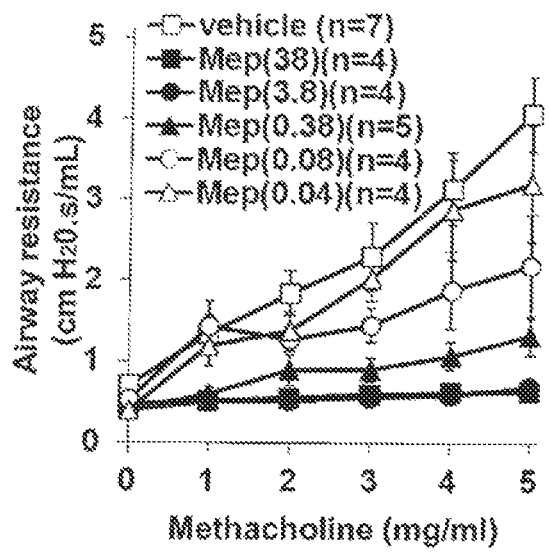
FIG. 11 shows a graph showing the results of measurement of airway resistance in the case of different doses of mepenzolate bromide being administered in Test Example 4.

The results were shown in FIG. 11.

Furthermore, mepenzolate was administered to the mice at a dose of 38 µg/kg. Then, the mice received five exposures to nebulized methacoline at 6 hours, 24 hours, and 48 hours after drug administration. The airway resistance for each time length was measured.

Figure 12:
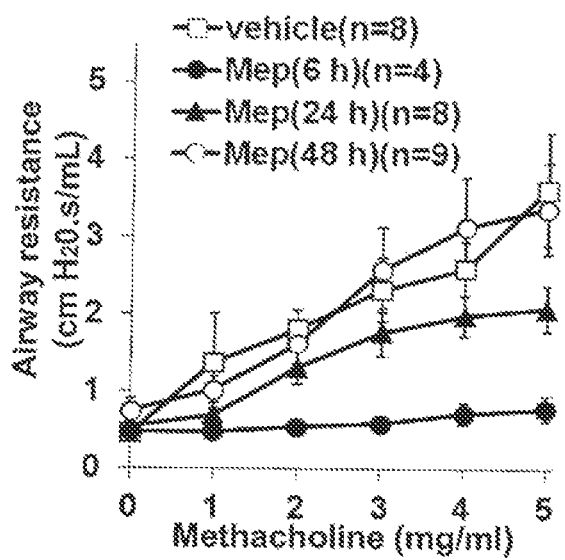
FIG. 12 shows a graph showing the results of measurement of airway resistance at different times after administration of mepenzolate bromide at a dose of 38 μg/kg in Test Example 4.

The results were shown in FIG. 12.

<Results>

As is found from the results shown in FIG. 11, mepenzolate reduced the airway resistance almost dose-dependently at doses of 0.04, 0.08, 0.38, 3.8, and 38.0 µg/kg.

As is found from the results shown in FIG. 12, mepenzolate reduced the airway resistance even 24 hours after administration thereof.

The above-mentioned results show that mepenzolate had an excellent effect on methacholine-induced airway resistance (airway constriction).

Test Example 5

Effect of Mepenzolate on Porcine Pancreatic Elastase-Induced Inflammation

<Method>

Different doses of mepenzolate were administered to 4 to 6 week old ICR mice once via the airway. 100 µg of porcine pancreatic elastase per mouse was administered one hour after administration of mepenzolate. Bronchoalveolar lavage fluid (BALF) was collected from the lung 24 hours after administration of porcine pancreatic elastase and a total cell count and a neutrophil count were measured. The results were shown in FIG. 13. Furthermore, the total number of TNF-α, MIP-2, MCP-1, or KC in the bronchoalveolar lavage fluid when 38 µg/kg of mepenzolate was administered via the airway was measured by an ELISA method. The results were shown in FIG. 14.

<Results>

Figure 13:
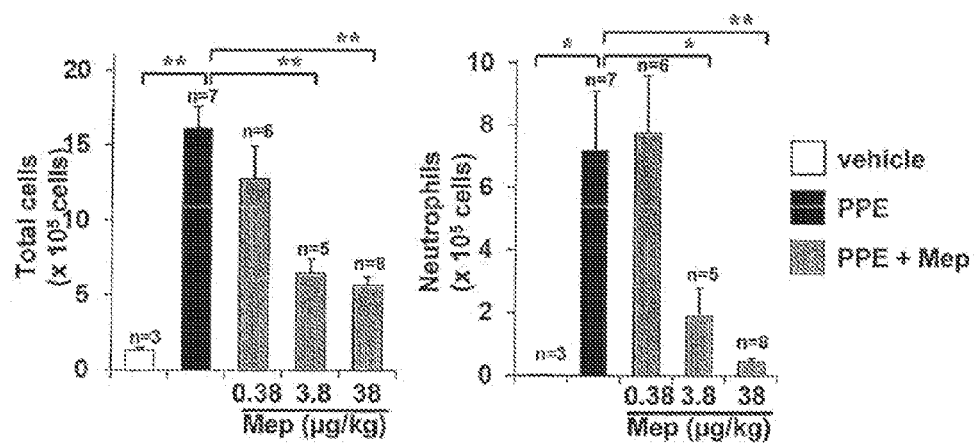
FIG. 13 shows graphs representing the results of measurement of a total cell count and a neutrophil count in Test Example 5.

As is found from the results shown in FIG. 13, the total cell count and the neutrophil count of the BALF decreased dependently on the dose of mepenzolate.

Figure 14:
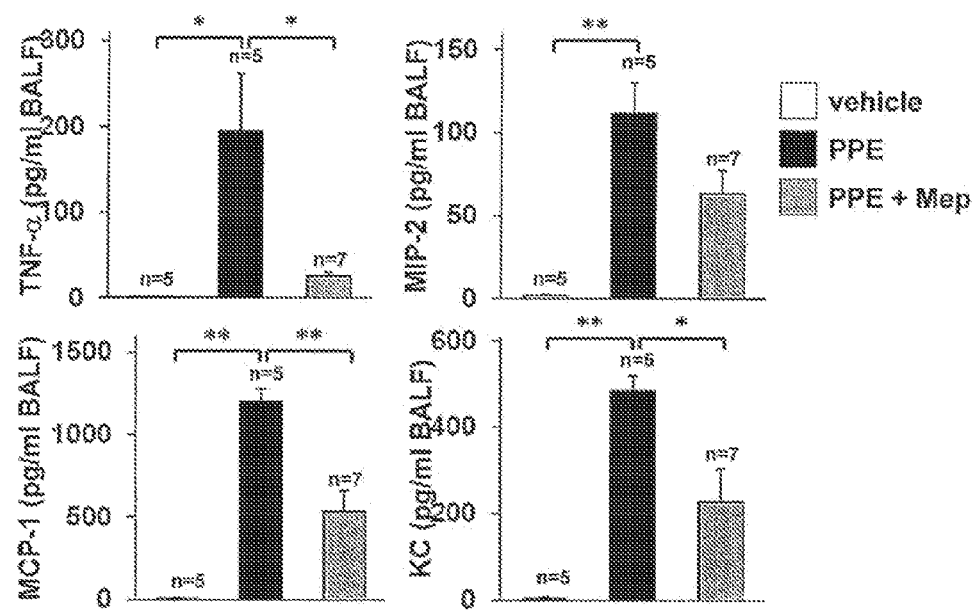
FIG. 14 shows graphs representing the results of measurement of TNF-α, MIP-2, MCP-1, and KC in Test Example 5.

As is found from the results shown in FIG. 14, the total number of TNF-α, MIP-2, MCP-1, or KC in the BALF decreased when 38 µg/kg of mepenzolate was administered.

It was found from the results described above that mepenzolate is effective against inflammatory symptoms caused by porcine pancreatic elastase.

Test Example 6

Effect of Mepenzolate on Pulmonary Emphysema and Altered Lung Function Resulting from Smoking <Method>

Three-times-a-day exposure to smoking and once-a-day coadministration of 38 µg/kg of mepenzolate were performed on 5 week old DBA/2 mice, 5 days a week (Monday to Friday) for 6 weeks. The mice were subjected to only smoking during the final week.

The mice were subjected to smoking by the method described below. 15 to 20 mice were placed in a 45 L chamber and the chamber was connected to a cigarette smoke generator. Commercially available unfiltered cigarette that produced 28 mg of tar and 2.3 mg of nicotine were used. The mice were exposed to smoke of one cigarette over 35 minutes, which was repeated three times a day for five days a week. This was continued for 6 weeks. The mice were made to inhale the cigarette smoke 15 times over a 5-minute period. Mepenzolate was administered to the mice by inhalation.

After smoking was completed, the mice were euthanized, sections of the lung tissues were prepared and dyed with H&E, and stained images were obtained by electron microscopy.

Figure 15:
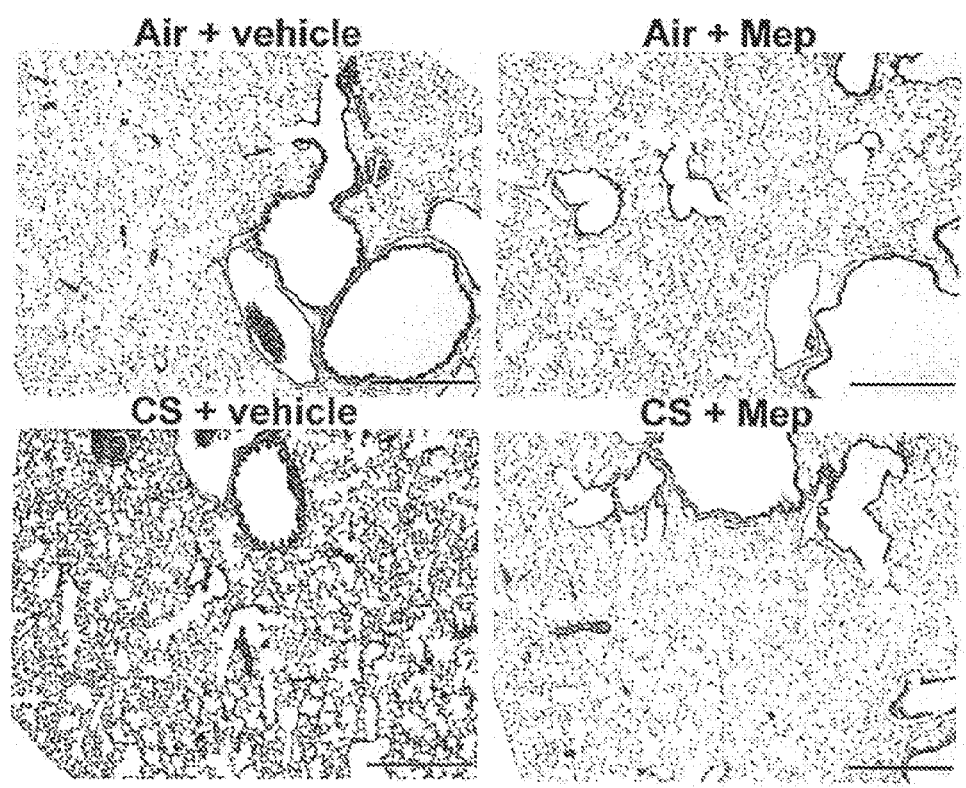
FIG. 15 shows electron micrographs of the lung tissues dyed with H&E in Test Example 6, in which the subjects were subjected to smoking.

The results were shown in FIG. 15 (scale bar: 500 µm).

The airspace size in the cells in the H&E stained images obtained above was measured as a mean linear intercept. The results were shown in FIG. 16.

Then, the total respiratory system elastance and the tissue elastance were measured by a similar method to that in Test Example 1. The results were shown in FIG. 17.

Figure 16:
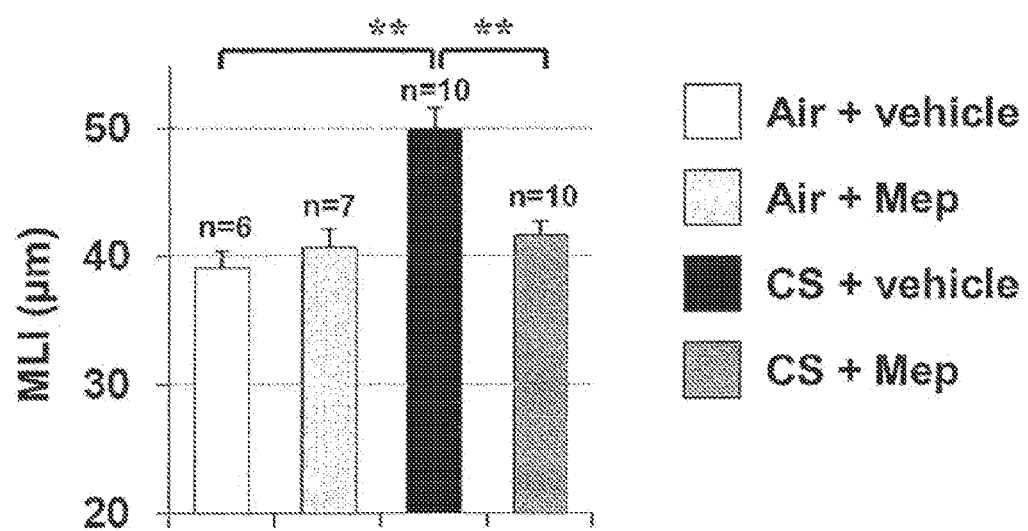
FIG. 16 shows a graph showing the results of measurement of a mean linear intercept in Test Example 6, in which the subjects were subjected to smoking.

In the figures, "CS" refers to cigarette smoke.
<Results>
As is found from the results shown in FIG. 15 and FIG. 16, the mean linear intercept was suppressed and damage in the alveolar wall was improved by administration of mepenzolate.

Figure 17:
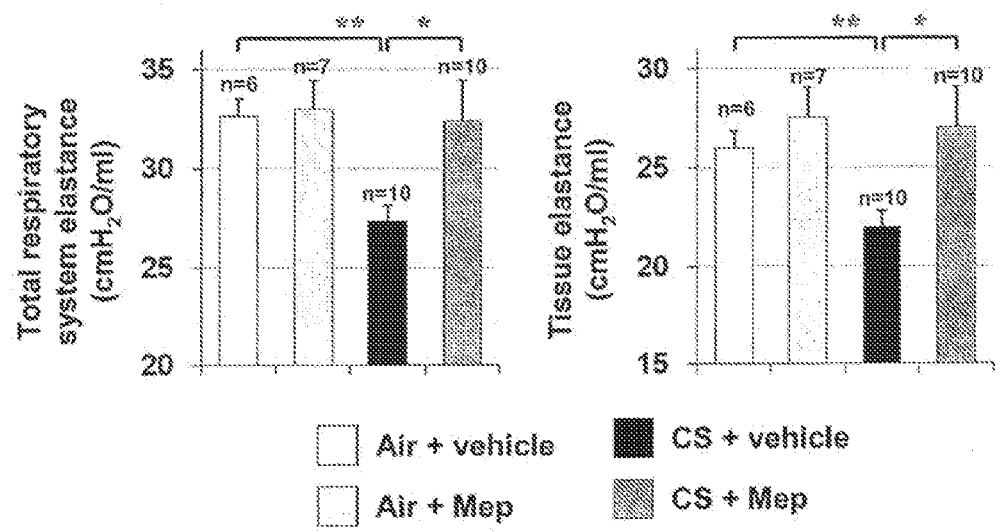
FIG. 17 shows graphs representing the results of measurement of total respiratory system elastance and tissue elastance in Test Example 6, in which the subjects were subjected to smoking.

As is found from the results shown in FIG. 17, the total respiratory system elastance and the tissue elastance were significantly improved by administration of mepenzolate.

It was found from the results described above that mepenzolate significantly improved damage in the lung resulting from smoking.

Test Example 7

Effect of Oral Administration of Mepenzolate on Porcine Pancreatic Elastase-Induced Pulmonary Emphysema and Altered Lung Function <Method>
100 μg of porcine pancreatic elastase per mouse was administered to 4 to 6 week old ICR mice once via the airway. Then, different doses (mg/kg) of mepenzolate were administered to the mice orally once daily for 14 days. After administration, sections of the lung tissues were excised. Subsequently, the sections were subjected to H&E dyeing, MLI measurement, and elastance measurement performed by a similar method to that in Test Example 1.

Figure 18:
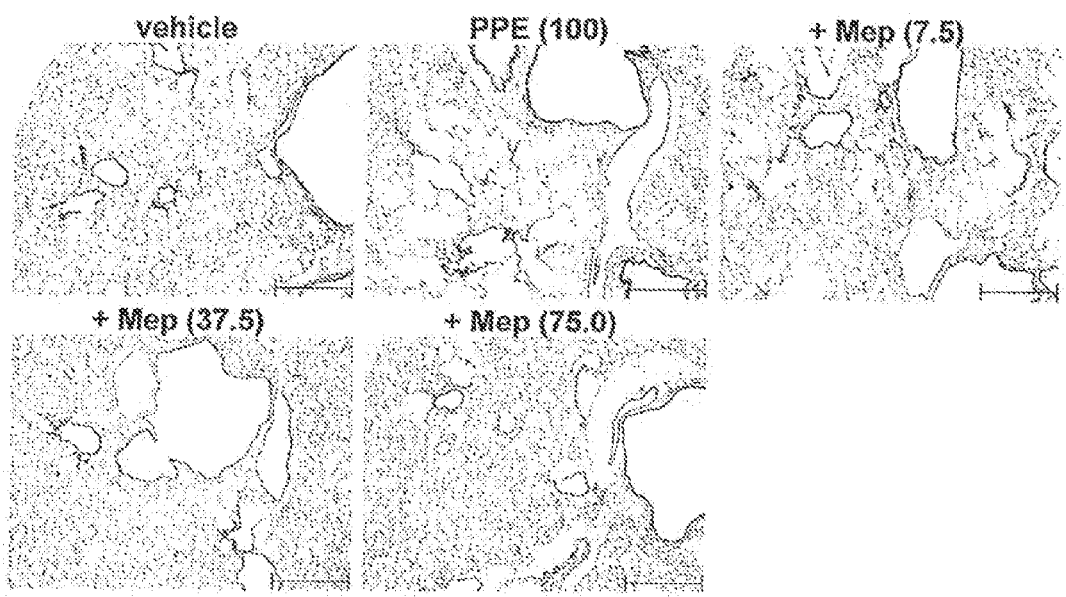
FIG. 18 shows electron micrographs of the lung tissues dyed with H&E in the case of oral administration in Test Example 7.
Figure 19:
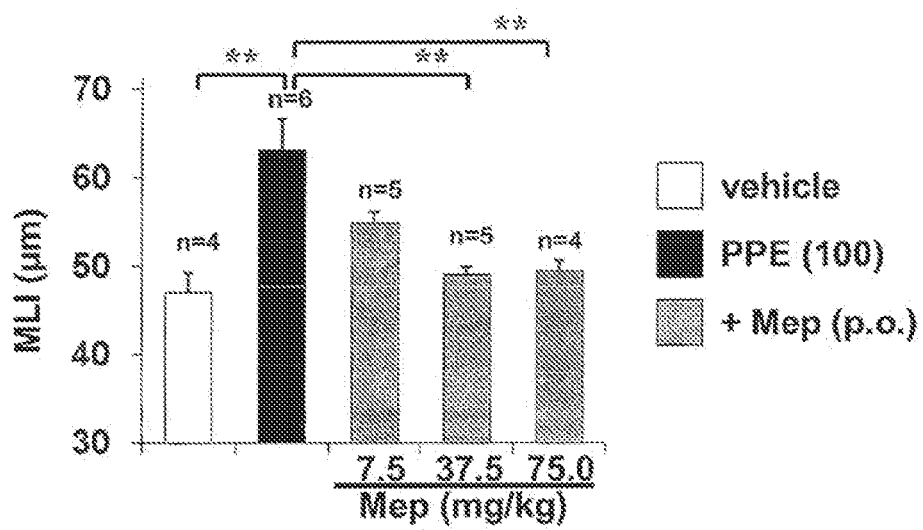
FIG. 19 shows a graph showing the results of measurement of a mean linear intercept in the case of oral administration in Test Example 7.
Figure 20:
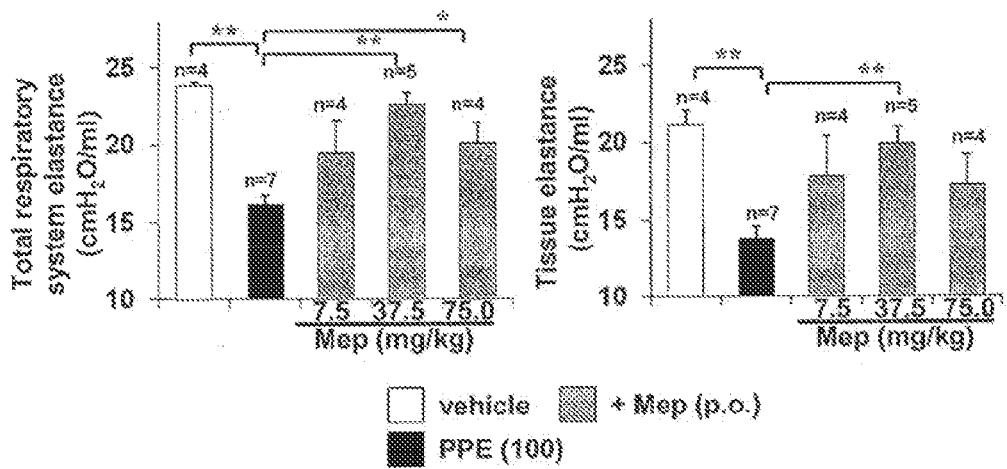
FIG. 20 shows graphs representing the results of measurement of total respiratory system elastance and tissue elastance in the case of oral administration in Test Example 7.

These results were shown in FIGS. 18 to 20.
<Results>
As is found from the results shown in FIGS. 18 to 20, it was found that oral administration of mepenzolate also improved damage in the lung.

Test Example 8

Effect of Rectal Administration of Mepenzolate on a Porcine Pancreatic Elastase-Induced COPD Model <Method>
100 μg of porcine pancreatic elastase per mouse was administered to 4 to 6 week old ICR mice once via the airway to induce damage in the lung.

Different concentrations of mepenzolate were administered intrarectally once daily. The alveolar lavage fluid was collected 3 days later and the total cell count was counted. The neutrophil count was also counted by dyeing the cells by a Diff-Quick technique.

Figure 21:
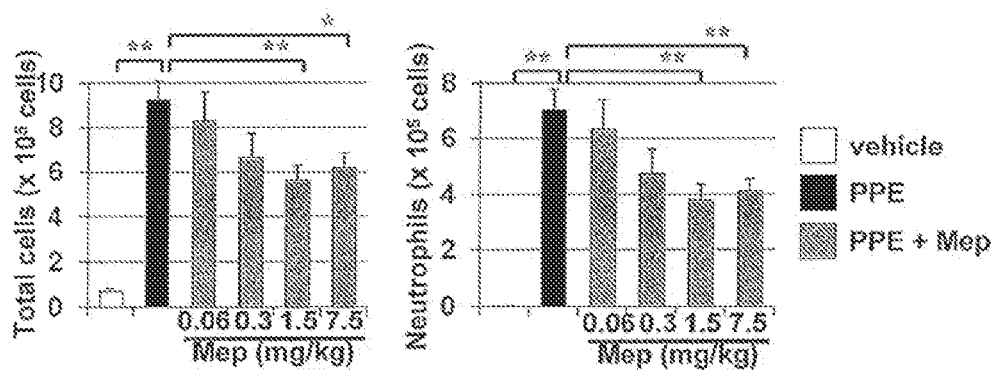
FIG. 21 shows graphs representing the results of measurement of a total cell count and a neutrophil count in the case of rectal administration in Test Example 8.

The results were shown in FIG. 21.

Furthermore, different doses (mg/kg) of mepenzolate were administered to the mice intrarectally once daily for 14 days. After administration, sections of the lung tissues were excised. Subsequently, the sections were subjected to H&E dyeing, MLI measurement, and elastance measurement performed by a similar method to that in Test Example 1.

Figure 22:
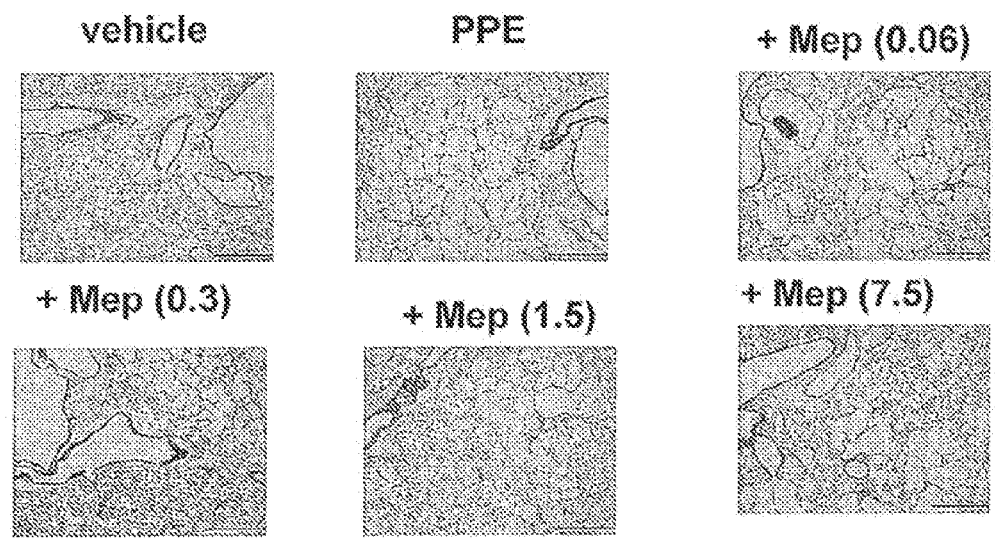
FIG. 22 shows electron micrographs of the lung tissues dyed with H&E in the case of rectal administration in Test Example 8.
Figure 23:
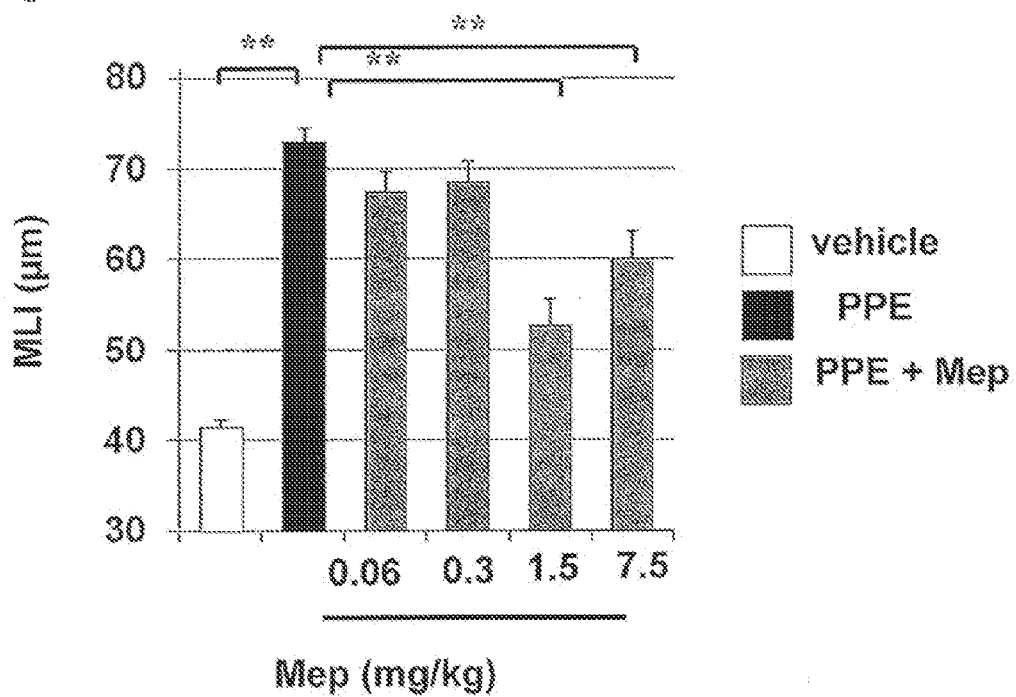
FIG. 23 shows a graph showing the results of measurement of a mean linear intercept in the case of rectal administration in Test Example 8.
Figure 24:
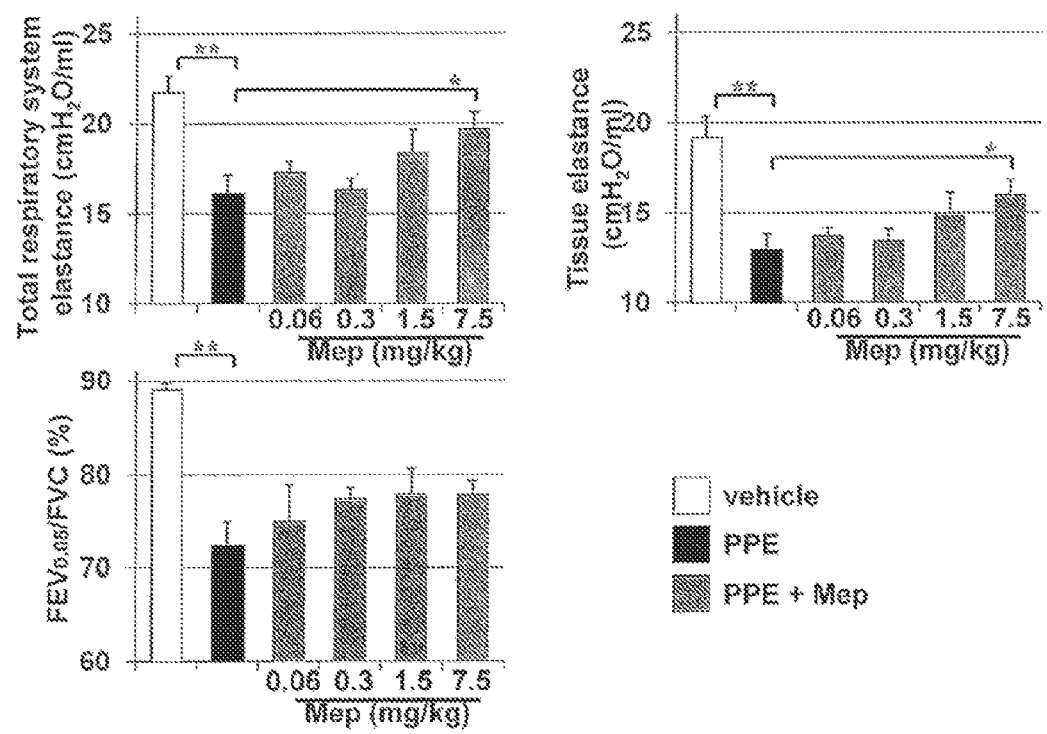
FIG. 24 shows graphs representing the results of measurement of total respiratory system elastance, tissue elastance, and $FEV_{0.05}/FVC$ in the case of rectal administration in Test Example 8.

These results were shown in FIGS. 22 to 24.
<Results>
As is found from the results shown in FIG. 21, decrease in the inflammatory cells was observed when mepenzolate was administered intrarectally and mepenzolate was found to have a significant anti-inflammatory effect.

Furthermore, as is found from the results shown in FIGS. 22 to 24, it was found that rectal administration of mepenzolate also improved damage in the lung induced by elastase.

Test Example 9

Effect of Rectal Administration of Mepenzolate on Methacoline-Induced Airway Constriction <Method>
Different doses (mg/kg) of mepenzolate were administered intrarectally and airway resistance induced by methacoline was measured by a similar method to that in Test Example 4.

Figure 25:
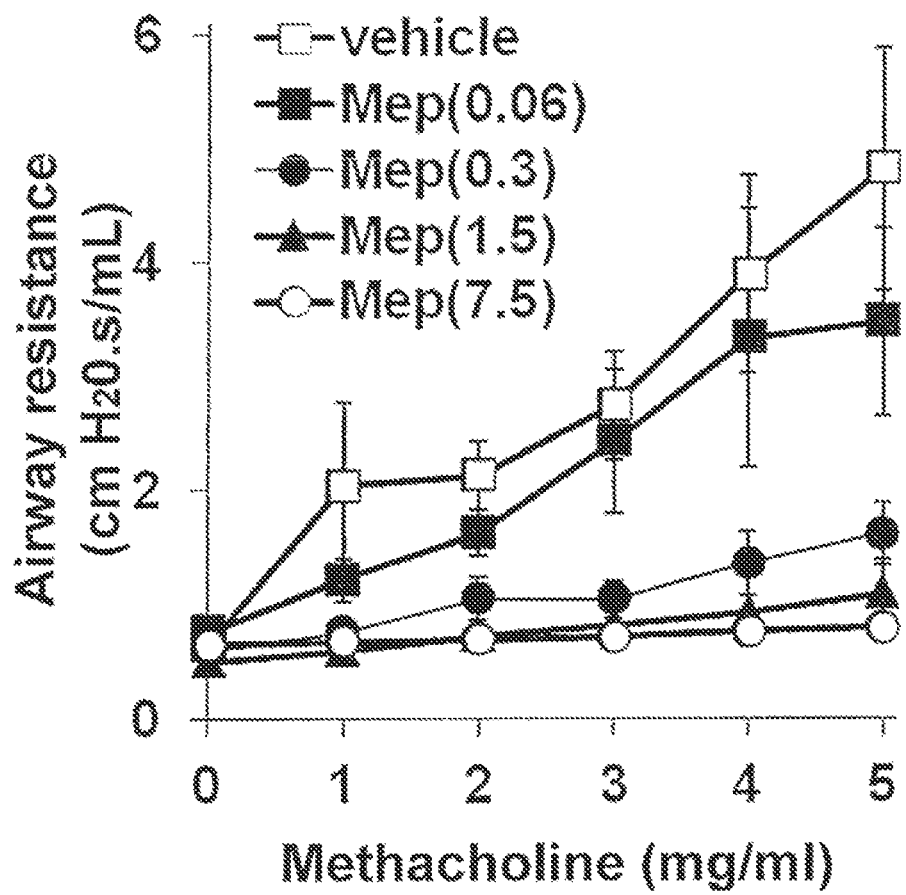
FIG. 25 shows a graph showing the results of measurement of airway resistance in the case of different doses of mepenzolate bromide being administered rectally in Test Example 9.

The results were shown in FIG. 25.
<Results>
As is found from the results shown in FIG. 25, rectal administration of mepenzolate also showed an excellent effect on the airway resistance induced by methacoline.

Hereinbelow, exemplary specific formulations of the agent for ameliorating COPD of the present invention are described.

Working Example 1

Inhalation Formulation

A liquid formulation for inhalation is prepared by mixing 1% (w/w) of mepenzolate bromide, 0.05% (w/w) of benzalkonium chloride, 10% (w/w) of polyethylene glycol, 20% (w/w) of propylene glycol, and the remaining percentage of purified water.

Working Example 2

Tablet

| | |
|---|---|
| Mepenzolate bromide | 50 mg |
| Lactose | 146 mg |
| Hydroxypropylcellulose | 150 mg |
| Magnesium Stearate | 4 mg |

Based on the formulation described above, granules were prepared and then the granules were compressed to prepare tablets each weighing 350 mg by a conventional method.

Working Example 3

Enema Preparation

An enema preparation was prepared by dissolving 1 mg of mepenzolate bromide in 1 mL of water and adding adequate amounts of carboxymethylcellulose sodium and tris(hydroxymethyl)aminomethane thereto.

INDUSTRIAL APPLICABILITY

As described above, the agent for ameliorating COPD provided by the present invention contains mepenzolate bromide, which has already been used in a clinical setting, as an active ingredient. The inventive agent exhibited a remarkable effect of ameliorating COPD by airway administration and inhalation administration, and also exhibited an effect of ameliorating COPD by oral administration and rectal administration. Mepenzolate bromide can be used without concern about side effects and without anxiety since the safety thereof has already been confirmed. Therefore, the medical value thereof is great.

The invention claimed is:

1. A method for ameliorating bronchoconstriction and bronchoinflammation in a subject having obstructive pulmonary disease, comprising administering a composition comprising mepenzolate bromide, to the subject wherein the composition is a powder, a solution, or suspension suitable for airway administration or inhalation wherein the mepenzolate bromide is administered in an amount sufficient to ameliorate both bronchoconstriction and bronchoinflammation in the subject.

2. The method of claim 1 wherein the composition is administered to the subject's airway or by inhalation.

3. A method for ameliorating obstructive pulmonary disease, comprising administering a composition comprising mepenzolate bromide as an active ingredient to a subject in need thereof, wherein the subject in need thereof has obstructive pulmonary disease and wherein the composition is administered orally or rectally.

4. The method of claim 1 wherein the excipient is one or more of an additive, an antiseptic, a solubilizer, a buffering agent, an isotonic agent, an absorption promoter, a thickener, or a propellant.

* * * * *